United States Patent [19]

Millauer et al.

[11] Patent Number: 4,469,641

[45] Date of Patent: Sep. 4, 1984

[54] OMEGA-FLUOROSULFATO-PERFLUORO-(2-METHYL-ALKAN-3-ONES)

[75] Inventors: Hans Millauer, Eschborn; Werner Schwertfeger, Butzbach; Günter Siegemund, Hofheim am Taunus, all of Fed. Rep. of Germany

[73] Assignee: Hoechst Aktiengesellschaft, Frankfurt am Main, Fed. Rep. of Germany

[21] Appl. No.: 496,628

[22] Filed: May 20, 1983

Related U.S. Application Data

[62] Division of Ser. No. 300,917, Sep. 10, 1981, abandoned.

[30] Foreign Application Priority Data

Sep. 12, 1980 [DE] Fed. Rep. of Germany ....... 3034499

[51] Int. Cl.³ .......................................... C07C 141/00
[52] U.S. Cl. .............................. 260/458 F; 260/543 F

[58] Field of Search ..................................... 260/458 F

[56] References Cited

U.S. PATENT DOCUMENTS 4,208,466 6/1980 Szur ................................. 260/458 F Primary Examiner—Nicky Chan
Attorney, Agent, or Firm—Curtis, Morris & Safford

[57] ABSTRACT

Omega-fluorosulfato-perfluoro-(2-methyl-alkan-3-ones) of the formula

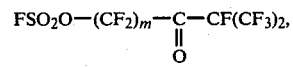

$$FSO_2O-(CF_2)_m-\underset{\underset{O}{\|}}{C}-CF(CF_3)_2,$$

which are intermediates in the preparation of perfluoro-isopropylketocarboxylic acid fluorides from omega-hydro-perfluoro-(2-methyl-alkan-3-ones).

3 Claims, No Drawings

OMEGA-FLUOROSULFATO-PERFLUORO-(2-METHYL-ALKAN-3-ONES)

This is a division of application Ser. No. 300,917 filed Sept. 10, 1981, now abandoned.

Perfluoroisopropylketocarboxylic acid fluorides are intermediates for the preparation of perfluorinated ketocarboxylic acid esters which have an isopropyl radical adjacent to the keto group and are in turn, inter alia, valuable heat transfer fluids and surface-active agents which are stable to chemicals and heat (compare, for example, Japanese preliminary published application Sho-54-163521).

These perfluoroisopropylketocarboxylic acid esters have the structure II. According to known processes, they are prepared by alcoholysis of perfluoroisopropylketocarboxylic acid fluorides of the formula I (Zh. Org. Khim. 11, 1626 (1975))

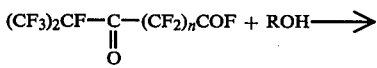

I

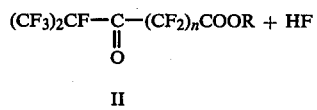

II in which R denotes alkyl and n denotes a number from 2 to 5.

Another process, which, however, is restricted only to n=0, uses fluoroglyoxalic acid esters for the preparation, these compounds being reacted with hexafluoropropene (Japanese preliminary published application Sho-54-163521):

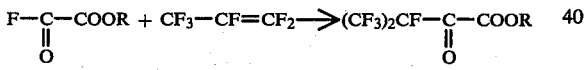

In addition to the restriction to the case where n=0, this process has the disadvantage that fluoroglyoxalic acid esters are obtained only in unsatisfactory yields. For example, according to German Offenlegungsschrift No. 2,751,050, fluoroglyoxalic acid methyl ester is formed in a yield of only about 10%.

On the other hand, perfluoroisopropylketocarboxylic acid fluorides of the formula I in which n=a number from 2 to 5 have been prepared by reacting perfluorodicarboxylic acid difluorides III with hexafluoropropene [Zh. Org. Khim. 11, 1626 (1975)].

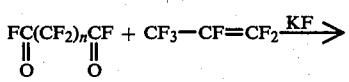

III

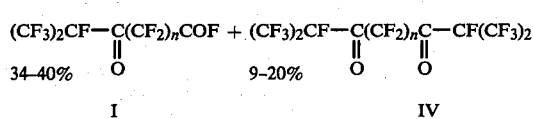

I          IV in which n denotes a number from 2 to 5. Apart from the fact that the diketones of the formula IV, which can be formed in yields of up to 20%, impair the yield of the desired products of the formula I and furthermore cannot be converted into these products by a subsequent reaction, the dicarboxylic acid fluorides of the formula III used as precursors are obtained only in a very low yield.

According to the process described in German Offenlegungsschrift No. 2,635,312, such perfluorinated dicarboxylic acid difluorides are obtained from perfluoroalkane-diiodides with oleum. The preparation of the perfluorodicarboxylic acid difluoride III in which n=2 from perfluorobutyl diiodide is described:

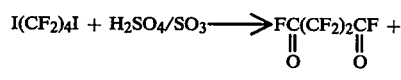

5-11%

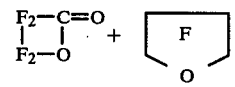

chiefly perfluoro-γ-butyrolactone and perfluorotetrahydrofuran being formed, in addition to 5-11% of the desired compound.

In the process of the Japanese authors I. Watanabe et al., reviewed in C.A. Volume 85, page 591 No. 85: 93867 f (1976), perfluorocycloalkenes are used as the starting materials and are converted into the desired compounds III in which n=a number from 2 to 4 with oxygen/ozone. In this case also, the yields are unsatisfactory, as the example for n=2 shows:

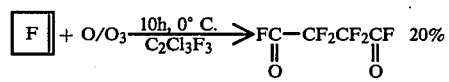

III in which n = 2

Because of the great importance of perfluoroisopropylketocarboxylic acid fluorides as precursors for the industrially important perfluoroisopropylketocarboxylic acid esters and because the processes for their preparation cannot be satisfactorily realized in industry, there was thus the object of opening up an improved route to perfluoroisopropylketocarboxylic acid fluorides which leads uniformly to the desired products in higher yields.

According to the invention, it was possible to achieve this object by providing new perfluoro compounds, that is to say ω-fluorosulfatoperfluoro-(2-methyl-alkan-3-ones) of the formula V:

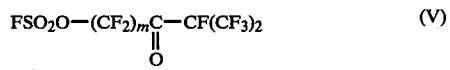

in which m denotes a number from 1 to 10, preferably 1 to 8 and in particular 1 to 6.

Starting from V, the perfluoroisopropylketocarboxylic acid fluorides of the formula I are obtained by decomposition in the presence of catalytic amounts of an alkali metal fluoride and in the absence of aprotic polar solvents. The perfluorinated ketocarboxylic acid fluorides of the formula I:

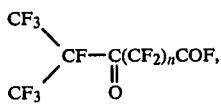

$$\begin{array}{c}CF_3\\ \phantom{xx}\diagdown\\ \phantom{xxxx}CF-C(CF_2)_nCOF,\\ \phantom{xx}\diagup\phantom{xxx}\|\\ CF_3\phantom{xxx}O\end{array} \qquad I$$

in which n denotes a number from 0 to 9, preferably 0 to 7 and in particular 0 to 5, are thus obtained from the compounds V in high yields.

According to the invention, the compounds of the formula I are prepared by (a) electrolyzing ω-hydro-perfluoro-(2-methyl-alkan-3-ones) of the formula VI

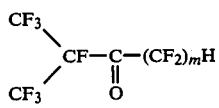

$$\begin{array}{c}CF_3\\ \phantom{xx}\diagdown\\ \phantom{xxxx}CF-C-(CF_2)_mH\\ \phantom{xx}\diagup\phantom{xxx}\|\\ CF_3\phantom{xxx}O\end{array} \qquad VI$$

in which m has the same meaning as in formula V, in an electrolyte consisting of fluorosulfonic acid and an alkali metal fluorosulfonate, using anodes made of metals of the platinum group (osmium, iridium or platinum) and/or glassy carbon, and cathodes made of a material which is customary, but stable under the electrolysis conditions, isolating the Ω-fluorosulfato-perfluoro-(2-methyl-alkan-3-ones) thereby formed, of the formula V

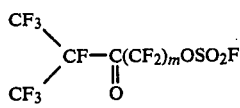

$$\begin{array}{c}CF_3\\ \phantom{xx}\diagdown\\ \phantom{xxxx}CF-C(CF_2)_mOSO_2F\\ \phantom{xx}\diagup\phantom{xxx}\|\\ CF_3\phantom{xxx}O\end{array} \qquad V$$

in which m has the abovementioned meaning, and (b) decomposing these compounds in the presence of catalytic amounts of an alkali metal fluoride MF, in which M can be Li, Na, K, Rb or Cs, and in the absence of polar aprotic solvents to give the perfluoroisopropylketocarboxylic acid fluorides of the formula I.

Although perfluorinated fluorosulfato compounds have already been prepared by anodic oxidation, for example Ω-fluorosulfatoperfluoroalkanes have been prepared in a mixture of fluorosulfonic acid and an alkali metal fluorosulfonate using platinum electrodes (J.C.S. Chem. Comm. 1978, 118), it is surprising, from the point of view of carrying out process stage a virtually without complications, that the keto function of the ω-hydroperfluoro-(2-methyl-alkan-3-ones) of the formula VI is not attacked during the electrolysis and thus is unchanged.

The smooth decomposition of the compounds of the formula V according to the invention in process stage b in the presence of catalytic amounts of an alkali metal fluoride to give the perfluoroisopropylketocarboxylic acid fluorides of the formula I was also surprising, since it is known, from Izv. Akad. Nauk SSSR, Ser. Khim. 1979, 3, 667-9, that the fluorosulfato radical is not split off in the presence of keto groups, but rearrangement takes place.

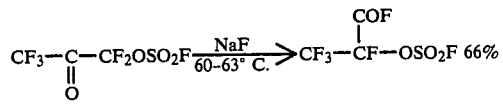

$$CF_3-C-CF_2OSO_2F \xrightarrow[60-63^\circ C.]{NaF} CF_3-CF-OSO_2F \quad 66\%$$

The starting compounds for the process according to the invention—that is to say the ω-H-perfluoro-(2-methyl-yl-alkan-3-ones) of the formula VI—can be prepared by the following known procedure by reaction of ω-hydroperfluorocarboxylic acid fluorides VII with hexafluoropropene in the presence of an alkali metal fluoride and acetonitrile:

$$H(CF_2)_mCOF + CF_3CF=CF_2 \xrightarrow[CH_3CN]{KF}$$
VII

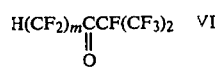

$$H(CF_2)_m\underset{\|}{\underset{O}{C}}CF(CF_3)_2 \quad VI$$

[I. P. Kolenko et al., reviewed in C.A. 82, 97627 p (1975)].

The ω-hydroperfluorocarboxylic acid fluorides can in turn be prepared in a manner which is known from the literature:

1. J. Am. Chem. Soc. 74, 1426 (1952):

The triazine derivative below is prepared from ammonia and tetrafluoroethylene in the presence of copper acetate:

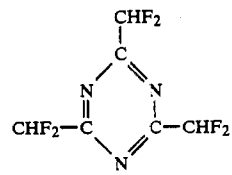

and sodium difluoroacetate can be obtained from this compound by heating with aqueous sodium hydroxide solution, and the acid fluorides of the formula VII in which m=1 are obtainable from the difluoroacetate by known methods.

2. U.S. Pat. No. 2,559,629 describes the preparation of aliphatic polyfluorocarboxylic acids and their salts by oxidation of polyfluoroalkanols with potassium permanganate:

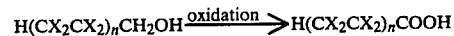

$$H(CX_2CX_2)_nCH_2OH \xrightarrow{oxidation} H(CX_2CX_2)_nCOOH$$

X=Cl or F, and at least half of the radicals X=F, and n=a number from 1 to 3.

The starting compounds for this oxidation are prepared from ethylene derivatives $CX_2=CX_2$ and methanol.

The acid fluorides are obtained from the resulting free acids by a known route; the compounds in which the radicals X=F are the compounds of the formula VII in which m=an integer.

3. J. Org. Chem. 42, 25, 4055 (1977) describes, inter alia, the following reaction:

$$H(CF_2)_6CH_2OH \xrightarrow{oxidation} H(CF_2)_6COOH \xrightarrow[reflux]{C_6H_5-COCl}$$

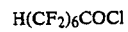

$$H(CF_2)_6COCl$$

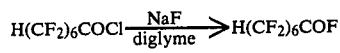

$$H(CF_2)_6COCl \xrightarrow[diglyme]{NaF} H(CF_2)_6COF$$

Process stage a—the electrolysis of the process according to the invention—is in principle carried out in the manner known, for example, from J.C.S., Chem. Comm. 1978, 118.

To prepare the base electrolyte, which, according to the invention, consists of fluorosulfonic acid and an alkali metal fluorosulfonate dissolved therein, a corresponding, readily accessible alkali metal chloride, such as, for example, lithium chloride, sodium chloride or potassium chloride, is dissolved in fluorosulfonic acid, which, if necessary, has first been subjected to purification by fractional distillation, most of the hydrogen chloride immediately escaping from the solution. The remainder is driven out by introduction of dry nitrogen. The concentration of alkali metal sulfonate to be used in the base electrolyte is not critical and is in the range from about 0.05 to 3 moles per liter.

The starting substances of the formula VI are dissolved or dispersed in the base electrolyte, it being possible to use mixtures containing up to about 60%, relative to the base electrolyte.

Osmium, iridium, platinum or platinum alloys containing up to about 10% of other noble metals, for example iridium, are suitable as the anode. However, the anode preferably consists of glassy carbon, which has proved to be particularly corrosion-resistant under the electrolysis conditions. Glassy carbon is also suitable as the cathode, although the question of a material for this electrode is not critical and other substances, such as, for example, platinum, copper or high-grade steel, are likewise suitable.

The ratio of the anode area to cathode area is between about 1:1 and about 10:1, preferably between about 5:1 and about 10:1.

The electrolysis is carried out at an anodic current density of about 10–150 mA.cm$^{-2}$, preferably about 20–80 mA.cm$^{-2}$, and at a temperature of about 0° to 100° C., preferably about 20° to 40° C.

Working up of the electrolysis mixtures and isolation of the ω-fluorosulfato-perfluoro-(2-methyl-alkan-3-ones) of the general formula V are carried out in a manner known per se. In the case of two-phase reaction mixtures, it is advantageous to separate off the fluoro-organic phase, which in some cases still also contains a little fluorosulfonic acid, by decanting; otherwise, the electrolysis product must be separated off from the base electrolyte by distillation. In both cases, the electrolyte phase or the distillation bottom product can be recycled again into the electrolysis stage after the addition of fresh fluorosulfonic acid.

The crude ω-fluorosulfato-perfluoro-(2-methyl-alkan-3-ones) V can be further purified by fractional distillation. In certain circumstances it is advantageous to deacidify the crude products by prior treatment with sodium fluoride or washing out with sodium bicarbonate solution.

The second stage (b) of the process according to the invention comprises converting the ω-fluorosulfatoperfluoro-(2-methyl-alkan-3-ones) of the general formula V into the ω-fluorocarbonyl-perfluoro-(2-methyl-alkan-3-ones) of the general formula I in the presence of a suitable nucleophilic catalyst.

The alkali metal fluorides (LiF, NaF, KF, RbF and CSF) are catalysts for the process according to the invention. They can be employed either individually or as a mixture with one another. The amount of catalyst is in general between about 1 and 50 mole %, preferably between about 10 and 30 mole %, relative to the fluorosulfato compound of the formula V.

Depending on the catalyst used, the reaction temperatures are in general in the range between about −20° and +120° C., preferably between about 0° and +100° C.

The reaction can be carried out either under normal pressure or under increased pressure.

The sequence in which the reactants and, if appropriate, the solvent used are combined is of no importance for the conversion of the ω-fluorosulfatoperfluoro-(2-methyl-alkan-3-ones) of the formula V into the perfluoroisopropylketocarboxylic acid fluorides of the formula I in the manner according to the invention. However, it is advantageous to ensure that the batch is mixed thoroughly throughout the entire period of the reaction.

According to a preferred procedure, the catalyst is initially introduced, the ω-fluorosulfato-perfluoro-(2-methyl-alkan-3-one) of the formula V is added at room temperature and the reaction mixture is heated slowly until evolution of gas occurs. when the evolution of gas has ended, the perfluoroisopropylketocarboxylic acid fluoride of the formula I is separated off from the catalyst by distillation, using a column.

The following examples are intended to illustrate the invention in more detail.

A comparison of the preparation of an example of a perfluoroisopropylcarboxylic acid fluoride—that is to say of the compound

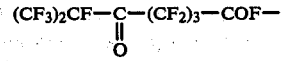

starting from simple base products via the corresponding ω-fluorosulfato compound according to the invention and in accordance with the state of the art then also follows. The route made possible by the invention gives a somewhat better overall yield in process stages which are in some cases simpler.

EXAMPLE 1

Preparation of 4-fluorosulfato-perfluoro-(2-methyl-butan-3-one)

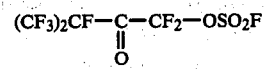

The electrolysis device comprises a cylindrical glass vessel which has an internal diameter of about 60 mm and is 100 mm in height and is provided with an outer cooling jacket and a lid. The cell is provided with a dry ice condenser acting as a reflux condenser, and also with a gas inlet tube, thermometer and the current leads for the electrodes. A cylindrical anode of platinum gauze (diameter: 40 mm; height: 40 mm; mesh width: about 1 mm), which is attached to the underneath of the cell lid, is located at a distance of about 20 mm from the bottom. A second cylinder of platinum gauze (diameter: 12 mm; height: 40 mm) is also held by the lid of the cell, and serves as the cathode. A bar magnet encased by PTFE on the bottom of the cell is utilized as a stirrer. The cell is cooled by an external cooling circulation using perchloroethylene as the cooling liquid.

All the parts of the device which come into contact with the medium are made of glass, platinum or PTFE.

The base electrolyte is prepared by adding 12.5 g (0.16 mole) of potassium chloride to 250 g of distilled fluorosulfonic acid; a colorless solution is formed and is freed from residual hydrogen chloride by introduction of dry nitrogen and then pre-electrolyzed at a current strength of 2 A for 4 hours. After addition of 85.5 g (0.34 mole) of 4-hydro-perfluoro-(2-methyl-butan-3-one), electrolysis is carried out at a current strength of 2 A and at a temperature of 25° C. until the charge which has been put through reaches 57 Ah. The cell voltage is 5-6 V.

When the electrolysis has ended, the electrolysis mixture is distilled up to a bottom temperature of 165° C. and the distillate (125 g) is subjected to further fractional distillation. 27.3 g (35% of theory, relative to the starting material reacted) of 4-fluorocarbonyl-perfluoro-(2-methyl-butan-3-one of boiling point 87°–88° C. are obtained as a fraction. $^{19}$F-NMR (CDCl$_3$)**: +50.8 (1F, —OSO$_2$F); −74.0 (6F, —CF$_3$); −78.0 (2F, —CF$_2$—); −191.5 (1F, >CF)

**CFCl$_3$ serves as the internal standard for all the $^{19}$F-NMR spectra.

EXAMPLE 2

Preparation of 3-fluorocarbonyl-perfluoro-(2-methyl-propan-3-one)

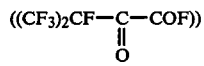

2.5 g (0.016 mole) of dry cesium fluoride are initially introduced into a 100 ml three-necked flask, which has been thoroughly dried by heating, with a magnetic stirrer, thermometer, dropping funnel and 20 cm Raschig ring column with a distillation head and low-temperature condenser. 30 g (0.08 mole) of 4-fluorosulfato-perfluoro-(2-methyl-butan-3-one) are then added at room temperature. During this addition, sulfuryl fluoride is evolved. After the mixture has been stirred at 22° C. for 3 hours, the product is separated off from the cesium fluoride by distillation. 11 g (0.045 mole) of 3-fluorocarbonyl-perfluoro-(2-methyl-propan-3-one) of boiling point 32°–33° C. under 753 mm are obtained, which corresponds to a yield of 56% of theory.

C$_5$F$_8$O$_2$ (molecular weight: 244); calculated: C 24.6%; F 62.2%; found: C 23.9%; F 59.8%.

$^{19}$F-NMR (CDCl$_3$): +27.2 (1F, COF); −73.3 (6F, —CF$_3$); −192.7 (1F, >CF)

EXAMPLE 3

Preparation of 5-fluorosulfato-perfluoro-(2-methyl-pentan-3-one)

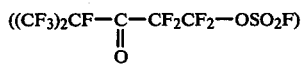

Using an electrolysis device and after preparation of a base electrolyte from 250 g of fluorosulfonic acid and 12.5 g (0.16 mole) of potassium chloride, as described in Example 1, 99 g (0.33 mole) of 5-hydroperfluoro-(2-methyl-pentan-one) are electrolyzed at a current density of 2 A and at a cell voltage of 6–11 V. The electrolysis temperature is 25° C. After a charge of 63 Ah has been put through, the electrolysis is ended and the reaction mixture is separated into its components in a separating funnel. The fluoro-organic phase (145 g) is subjected to fractional distillation on a 30 cm packed column. 84 g (84% of theory, relative to the starting material reacted) of 5-fluorosulfato-perfluoro-(2-methyl-pentan-3-one) of boiling point 104°–105° C. are obtained as a fraction.

$^{19}$F-NMR (CDCl$_3$): +15.7 (1F, —OSO$_2$F); −73.0 (6F, —CF$_3$); −83.4 (2F, —OCF$_2$—); −119.0 (2F, —CO—CF$_2$—); −189.4 (1F, >CF).

EXAMPLE 4

Preparation of 4-fluorocarbonyl-perfluoro-(2-methyl-butan-3-one)

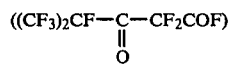

5 g (0.033 mole) of dry cesium fluoride are initially introduced into a 250 ml three-necked flask, which has been thoroughly dried by heating, with a magnetic stirrer, dropping funnel, thermometer and condenser (−20° C.) connected to a trap (−78° C.), and 92 g (0.23 mole) of 5-fluorosulfato-perfluoro-(2-methyl-pentan-3-one) are added, during which sulfuryl fluoride is evolved and the internal temperature rises from 24° to 30° C. After the mixture has been heated to 60° C., the evolution of gas increases. However, it stops within 20 minutes, and reflux is established. Subsequent distillation over a 50 cm Raschig ring column gives 51 g (0.173 mole) of 4-fluorocarbonyl-perfluoro-(2-methyl-butan-3-one) with a boiling point of 58° C. under 766 mm. (Yield: 75.6% of theory)

C$_6$F$_{10}$O$_2$ (molecular weight: 294); calculated: C 24.5%; F 64.6%; found: C 24.4%; F 63.6%.

$^{19}$F-NMR (CDCl$_3$): +24.3 (1F, —COF); −73.2 (6F, —CF$_3$); −111.0 (2F, —CF$_2$—); −190.8 (1F, >CF)

EXAMPLE 5

Preparation of 7-fluorosulfato-perfluoro-(2-methyl-heptan-3-one)

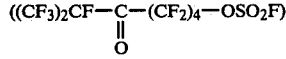

An electrolysis device as described in Example 1 is employed, but a plate (100×20×3 mm) of glassy carbon is used as the anode and a bar (diameter: 3 mm, length: 100 mm) of the same material is used as the cathode. After a base electrolyte has been prepared from 250 g of fluorosulfonic acid and 10.6 g (0.25 mole) of lithium chloride in a manner analogous to that described in Example 1 has been prepared, 185 g (0.46 mole) of 7-hydro-perfluoro-(2-methyl-heptan-3-one) are electrolyzed at a current density of 2 A and a cell voltage of 13–15 V for 15 hours. The electrolysis temperature is 20° C. The electrolysis mixture is then separated into its components in a separating funnel and the fluoro-organic phase (194 g) is subjected to fractional distillation on a 30 cm packed column. 124 g (66% of theory, relative to the starting material reacted) of 7-fluorosulfato-perfluoro-(2-methyl-heptan-3-one) of boiling point 143°–144° C. are obtained as a fraction.

$^{19}$F-NMR (CDCl$_3$): +51.5 (1F, —OSO$_2$F); −73.2 (6F, —CF$_3$); −82.8 (2F, —O—CF$_2$—); −116.4 (2F, —CF$_2$—); −120.7 (2F, —CF$_2$—); −123.3 (2F, —CF$_2$—); −190.2 (1F, >CF).

EXAMPLE 6

Preparation of 6-fluorocarbonyl-perfluoro-(2-methyl-hexan-3-one)

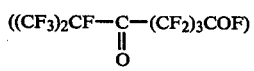

8 g (0.053 mole) of dry cesium fluoride and 223 g (0.45 mole) of 7-fluorosulfato-perfluoro-(2-methyl-heptan-3-one) are combined at room temperature in a 200 ml three-necked flask with a magnetic stirrer, 20 cm Raschig ring column and low-temperature distillation head, dropping funnel and thermometer, and the mixture is warmed to 75° C. Sulfuryl chloride thereby evolves and is condensed in a trap. (43 g=0.42 mole=93% of theory). Fractional distillation gives a fraction of 160 g (0.41 mole) of 6-fluorocarbonyl-perfluoro-(2-methyl-hexan-3-one) with a boiling of 102° C., which corresponds to a yield of 90% of theory.

$C_8F_{14}O_2$ (molecular weight: 394); calculated: C 24.36%; F 67.51%; found: C 24.1%; F 67.5%.

$^{19}F$-NMR (CDCl$_3$): +24.63 (1F, —COF); −74.01 (6F, —CF$_3$); −116.8 (2F, —CF$_2$—); −118 (2F, —CF$_2$—); −122.3 (2F, —CF$_2$—); −191 (1F, >CF).

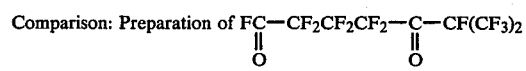

1. Via the ω-fluorosulfate compound

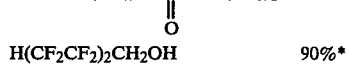 according to the invention

| | | |
|---|---|---|
|  | 90%* | |
| ↓ KMnO$_4$ | | |
| 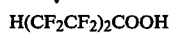 | 89%*, | according to J. Org. Chem. 30, 2,182 86% |
| ↓ C$_6$H$_5$—CCl$_3$ | | |
| 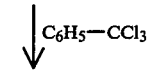 | 96%* | according to J. Org. Chem. 30, 2,182 46% |
| ↓ KF | | |
|  | 50%* | |
| ↓ | | |
|  | 66%* | according to the invention |
| ↓ | | |
|  | 90%* | according to the invention |
| ↓ | | |
| 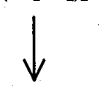 | | |

* = yields achieved in our own experiments.

Comparison: Preparation of 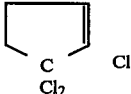

5 Yield relative to H(CF$_2$CF$_2$)$_2$CH$_2$OH: 22.8%.

2. According to the state of the art

| | | |
|---|---|---|
| 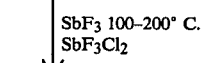 | 72.5% | Houben-Weyl 5/3 Page 190, J. Indian. Chem. Soc. 30 525 (1953) |
| ↓ SbF$_3$ 100–200° C. SbF$_3$Cl$_2$ | | |
| 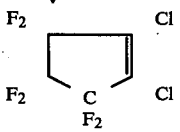 | 86% | J. Am. Chem. Soc. 67 1235 (1945) Houben-Weyl 5/3, page 369 (1962) |
| ↓ KMnO$_4$ | | |
| 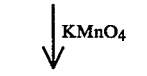 | 91% | Soviet Union author's certificate 216 690 |
| ↓ 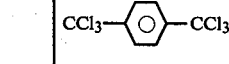 | | |
| 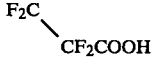 | 90%* | Analogous process |
| ↓ KF | | |
| 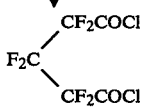 | 40% | Zh. Org. Khim. 11, 1626 (1975) |
| ↓ CF$_3$CF=CF$_2$ | | |
| 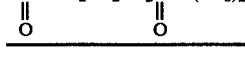 | | |

Overall yield, relative to perchlorocyclopentene: 20.4%.

We claim:

1. An ω-fluorosulfato-perfluoro-(2-methyl-alkan-3-one) of the formula

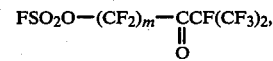

wherein m is 1 to 10.

2. A compound as in claim 1 wherein m is 1 to 8.
3. A compound as in claim 1 wherein m is 1 to 6.

* * * * *